United States Patent
Elomari

(10) Patent No.: US 7,569,740 B2
(45) Date of Patent: *Aug. 4, 2009

(54) ALKYLATION OF OLEFINS WITH ISOPARAFFINS IN IONIC LIQUID TO MAKE LUBRICANT OR FUEL BLENDSTOCK

(75) Inventor: Saleh Elomari, Fairfield, CA (US)

(73) Assignee: Chevron U.S.A. Inc., San Ramon, CA (US)

(*) Notice: Subject to any disclaimer, the term of this patent is extended or adjusted under 35 U.S.C. 154(b) by 707 days.

This patent is subject to a terminal disclaimer.

(21) Appl. No.: 11/316,157

(22) Filed: Dec. 20, 2005

(65) Prior Publication Data

US 2007/0142690 A1 Jun. 21, 2007

(51) Int. Cl.
*C07C 2/60* (2006.01)
*C07C 2/62* (2006.01)

(52) U.S. Cl. .................. 585/722; 585/728; 585/729

(58) Field of Classification Search .................. 585/722, 585/727, 728
See application file for complete search history.

(56) References Cited

U.S. PATENT DOCUMENTS

| 5,750,455 A | 5/1998 | Chauvin et al. |
| 6,028,024 A | 2/2000 | Hirschauer et al. |
| 6,395,948 B1 | 5/2002 | Hope et al. |
| 2001/0001804 A1 | 5/2001 | Skledar et al. |

FOREIGN PATENT DOCUMENTS

| EP | 0 791 643 | 8/1997 |

*Primary Examiner*—Thuan Dinh Dang
(74) *Attorney, Agent, or Firm*—Susan M. Abernathy; David M. Tuck

(57) ABSTRACT

A process and method for making a superior lubricant or distillate fuel component by the alkylation of $C_5+$ olefins with isoparaffins to produce a "capped" (alkylated) olefin using an acidic chloroaluminate ionic liquid catalyst system. Preferably the catalyst system includes a Brönsted acid.

20 Claims, No Drawings

ALKYLATION OF OLEFINS WITH ISOPARAFFINS IN IONIC LIQUID TO MAKE LUBRICANT OR FUEL BLENDSTOCK

BACKGROUND OF THE INVENTION

Olefin oligomers and relatively long chain olefins can be used in the production of fuel and lubricant components or blendstocks. One problem with the use of olefins in either of the above uses is that the olefinic double bond can be undesirable. Olefinic double bonds cause problems in both fuels and in lubricants. Olefins can oligomerize forming 'gum' deposits in the fuel. Olefins in fuel are also associated with air quality problems. Olefins can also oxidize which can be a particular problem in lubricants. One way of minimizing the problem is to hydrogenate some or all of the double bonds to form saturated hydrocarbons. A method of doing this is described in US published Application US 2001/0001804 which is incorporated by reference herein in its entirety.

Hydrogenation can be an effective way to minimize the concentration of olefins in the lubricant or fuel. However, hydrogenation requires the presence of hydrogen and a hydrogenation catalyst both of which can be expensive. Also excessive hydrogenation can lead to hydrocracking. Hydrocracking can increase as one attempts to hydrogenate the olefins to increasingly lower concentrations. Hydrocracking is generally undesirable as it produces a lower molecular weight material where it is generally desirable to produce a higher molecular weight material when producing fuels and lubricants from olefins. Directionally it would generally be preferred to increase, not decrease the average molecular weight of the material. Thus, using the hydrogenation method, it is desired to hydrogenate the olefins as thoroughly as possible while minimizing any hydrocracking or hydrodealkylation. This is inherently difficult and tends to be a compromise.

Hydrocracking of a slightly branched hydrocarbon material can also lead to less branching. Cracking tend to be favored at the tertiary and secondary centers. For example, a branched hydrocarbon can crack at a secondary center forming two more linear molecules which is also directionally undesirable.

Potentially, Ionic Liquid catalyst systems can be used for the oligomerization of olefins such as normal alpha olefins to make olefin oligomers. A Patent that describes the use of an ionic liquid catalyst to make polyalphaolefins is U.S. Pat. No. 6,395,948, which is incorporated herein by reference in its entirety. A published application that discloses a process for oligomerization of alpha olefins in ionic liquid catalysts is EP 791,643.

Ionic Liquid catalyst systems have also been used for isoparaffin—olefin alkylation reactions. Patents that disclose a process for the alkylation of isoparaffins by olefins are U.S. Pat. Nos. 5,750,455 and 6,028,024.

It would be desirable to have a process that can eliminate most or all of the double bonds (olefins) in a lubricant or distillate fuel starting material without the use of deep hydrogenation (using hydrogen and hydrogenation catalysts) while preferably maintaining or more preferably increasing the average molecular weight and branching of the material and without undesirable side reactions. The present invention provides a new process with just such desired features.

SUMMARY OF THE INVENTION

The present invention provides a process for making a fuel or lubricant component by the alkylation of olefins with an isoparaffin to "cap" (alkylate) at least a portion of the double bonds while increasing the degree of branching and the molecular weight of the product. In a particular embodiment, the present invention provides a process for making a distillate fuel or Lubricant component comprising contacting a stream comprising one or more $C_5+$ olefin feed and a stream comprising one or more isoparaffin feed with a catalyst comprising an acidic chloroaluminate ionic liquid in the presence of a Brönsted acid, at alkylation conditions, to form an effluent wherein at least 40 wt % of the effluent is capped olefin (paraffinic products).

The present invention provides a novel way to reduce the concentration of double bonds in an olefinic hydrocarbon and at the same time enhance the quality of the desired fuel or lubricant. The present invention also reduces the amount of hydrofinishing that is needed to achieve a desired product with low olefin concentration. The olefin concentration can be determined by Bromine index or Bromine number. Bromine Number can be determined by ASTM D 1159 test method. Bromine index can be determined by ASTM D 2710. Test methods D 1159 and ASTM D 2710 are incorporated herein by reference in their entirety. Bromine Index is effectively the number of milligrams of Bromine ($Br_2$) that react with 100 grams of sample under the conditions of the test. Bromine number is effectively the number of grams of bromine that will react with 100 grams of specimen under the conditions of the test.

The effluent from the alkylation of the present invention is a capped or partially capped olefin where an alkyl group has been added to the olefin and the olefin double bond has been eliminated. Said effluent should have a Bromine Number of less than 10, preferably less than 4, more preferably less than 3.

In a particular embodiment of the present invention the effluent is subjected to a hydrogenation step to further reduce the olefin content and hence the Bromine Number. The hydrogenation step can reduce the Bromine Number to less than 1, preferably less than 0.4, more preferably less than 0.2. A method of hydrogenation is described in US published Application US 2001/0001804 which is herein incorporated by reference in its entirety.

In a preferred embodiment of the present invention, HCl or a component that provides protons is added to the reaction mixture. Although not wishing to be limited by theory, it is believed that the presence of a Brönsted acid such as HCl greatly enhances the acidity and hence the activity of the ionic liquid catalyst system.

Among other factors, the present invention involves the surprising new way of making a lubricant base oil or fuel blendstock that has reduced levels of olefins without hydrogenation or with minimal hydrofinishing. The present invention also increases the value of the resultant alkylated ("capped") olefins by increasing the molecular weight of the capped olefins and increasing the branching. These properties can both add significant value to the product particularly when starting with a highly linear hydrocarbon such as one of the preferred feeds to the present invention (i.e. Fischer-Tropsch derived hydrocarbons). The present invention is based on the finding that an acidic chloroaluminate ionic liquid catalyst system in the presence of a Brönsted acid can be used to effectively alkylate an olefin or oligomerized olefin with an isoparaffin under relatively mild conditions and without substantial undesirable side reactions.

The catalyst system of the present invention is an acidic haloaluminate ionic liquid catalyst system and preferably chloroaluminate ionic liquid system. More preferably the acidic chloroaluminate ionic liquid system includes the presence of a Brönsted acid. Preferably the Brönsted acid is a halohalide such as HCl, HF, HBr and HI. Most preferably the Brönsted acid is HCl.

DETAILED DESCRIPTION OF THE INVENTION

The present invention provides a novel process for the production of fuel or lubricant components by the alkylation of olefins with isoparaffins in an ionic liquid medium to form a product having greatly reduced olefin content and improved quality. Amazingly, we have found that alkylation of relatively long chain alpha olefin with an isoparaffin can be done in ionic liquid catalyst system in the presence of a Bronsted acid. The alkylated or partially alkylated olefin stream that results has very desirable properties for use as a fuel or lubricant blendstock. In particular the present invention provides a process for making a distillate fuel, lubricant, distillate fuel component, lubricant component, or solvent having improved properties such as increased branching, higher molecular weight, and lower bromine number.

In the present application the term "capped" olefin means an alkylated or partially alkylated olefin where the double bond of the olefin has been removed and an alkyl group has been added.

The terms "distillate fuel, distillate fuel fraction, petroleum derived distillate" means a hydrocarbon with boiling points between about 250 degrees F. and 1100 degrees F., preferably 300 degrees F. and 700 degrees F. The preferred method to measure boiling ranges is with ASTM D 2887 or for materials with Final Boiling Points greater than 1000° F. ASTM D 6352. ASTM D 2887 and ASTM D 6352 are incorporated by reference in their entirety. The lower value of the boiling range is the Initial Boiling Point (IBP) and the higher value of the boiling range is the Final Boiling Point (FBP). While not preferred, ASTM D-86 and ASTM D1160 can be used, but their results must be converted to True Boiling Points (TBP) for comparison. The term "distillate" means that typical conventional fuels of this type can be generated from vapor overhead streams of petroleum crude distillation or Fischer-Tropsch derived hydrocarbons. In contrast, residual fuels cannot be generated from vapor overhead streams of petroleum crude distillation, and are a non-vaporizable remaining portion. Within the broad category of distillate fuels are specific fuels that include: naphtha, jet fuel, diesel fuel, kerosene, aviation gasoline, fuel oil, and blends thereof. Distillate fuel as used herein may mean distillate fuels prepared by Fischer Tropsch processes as well as distillate fuels generated from conventional petroleum crude distillation as appropriate in the context.

A salable distillate fuel is a distillate fuel meeting the specifications for one or more of naphtha, jet fuel, diesel fuel, kerosene, aviation gas, fuel oil, and blends thereof.

Ionic Liquids

Ionic liquids are a class of compounds made up entirely of ions, and are generally liquids at ambient temperatures. Often salts which are composed entirely of ions are solids with high melting points, for example, above 450 degrees C. These solids are commonly known as 'molten salts' when heated to above their melting points. Sodium chloride, for an example, is a common "molten salt" with a melting point of 800 degree C. Ionic liquids differ from 'molten salts', in that they have low melting points, for example, from −100 degrees C. to 200 degree C. Ionic liquids tend to be liquids over a very wide temperature range, with some having a liquid range of up to about 300 degrees C. or higher. Ionic liquids are generally non-volatile, with effectively no vapor pressure. Many are air and water stable, and can be good solvents for a wide variety of inorganic, organic, and polymeric materials.

The properties of ionic liquids can be tailored by varying the cation and anion pairing. Ionic liquids and some of their commercial applications are described, for example, in J. Chem. Tech. Biotechnol, 68:351-356 (1997); J. Phys. Condensed Matter, 5:(supp 34B):B99-B106 (1993); Chemical and Engineering News, Mar. 30, 1998, 32-37; J. Mater. Chem., *:2627-2636 (1998); and Chem. Rev., 99:2071-2084 (1999), the contents of which are hereby incorporated by reference.

Many ionic liquids are amine based. Most commonly used ionic liquids are those formed by reacting a nitrogen-containing heterocyclic ring (cyclic amines), preferably nitrogen-containing aromatic rings (aromatic amines), with an alkylating agent (for example, an alkyl halide) to form a quaternary ammonium salt, followed by ion exchange with Lewis acids and halide salts or anion metathesis reactions with the appropriate anion sources to form ionic liquids. Examples of suitable aromatic amines include pyridine and its derivatives, imidazole and its derivatives, and pyrrole and its derivatives. These amines can be alkylated with varying alkylating agents to incorporate a broad range of alkyl groups on the nitrogen including straight, branched or cyclic $C_{1-20}$ alkyl group, but preferably $C_{1-12}$ alkyl groups since alkyl groups larger than $C_1$-$C_{12}$ may produce undesirable solid products rather than ionic liquids. Pyridinium and imidazolium-based ionic liquids are perhaps the most commonly used ionic liquids. Other amine-based ionic liquids including cyclic and non-cyclic quaternary ammonium salts are frequently used. Phosphonium and sulphonium-based ionic liquids have also been used.

Counterions which have been used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, antimony hexafluoride, copper dichloride anion, zinc trichloride anion, as well as various lanthanum, potassium, lithium, nickel, cobalt, manganese, and other metal ions. The ionic liquids used in the present invention are preferably acidic.

The amine-based cation in the ionic liquid in the present invention can be selected from the group consisting of pyridinium- and imidazolium-based cations. Cations that have been found to be particularly useful in the process of the present invention include pyridinium-based cations.

Preferred ionic liquids that can be used in the process of the present invention include acidic chloroaluminate ionic liquids. Preferred ionic liquids used in the present invention are acidic pyridinium chloroaluminates. More preferred ionic liquids useful in the process of the present invention are alkyl-pyridinium chloroaluminates. Still more preferred ionic liquids useful in the process of the present invention are alkyl-pyridinium chloroaluminates having a single linear alkyl group of 2 to 6 carbon atoms in length. One particular ionic liquid that has proven effective is 1-butylpyridinium chloroaluminate.

In a more preferred embodiment of the present invention, 1-butyl-pyridnium chloroaluminate is used in the presence of Brönsted acid. Not to be limited by theory, the Brönsted acid acts as a promoter or co-catalyst. Examples of Brönsted acids are Sulfuric, HCl, HBr, HF, Phosphoric, HI, etc. Other protic acids and species that may serve as a source of protons can also be used.

The Feeds

In the process of the present invention, one of the important feedstocks comprises a reactive olefinic hydrocarbon. The olefinic groups provide the reactive sites for the oligomerization and alkylation reactions. In the process of the present invention, the olefinic hydrocarbon can be a fairly pure olefinic hydrocarbon cut or can be a mixture of hydrocarbons having different chain lengths and, thus, a wide boiling range. The olefinic hydrocarbon can be terminal olefin (an alpha olefin) or can be internal olefin (internal double bond). The olefinic hydrocarbon can be either straight chain or branched or a mixture of both. The feedstocks useable in the present invention can include an unreactive diluent such as normal paraffins.

Preferred olefin streams useful as feeds to the process of the present invention are olefins that are approximately of a sufficient molecular weight to be a desirable lubricant of distillate fuel component keeping in mind that the alkylation reaction of the present invention will increase both the molecular weight and the degree of branching of the product In one embodiment of the present invention, the olefinic feed comprises a mixture of mostly linear olefins of $C_5$ and above. The olefins are mostly but not entirely alpha olefins.

In another embodiment of the present invention, the olefinic feed can comprise at least 50% of a single alpha olefin species.

In another embodiment of the present invention, the olefinic feed can be comprised of an NAO cut from a high purity Normal Alpha Olefin (NAO) process made by ethylene oligomerization.

In an embodiment of the present invention, some or all of the olefinic feed to the process of the present invention comprises thermally cracked hydrocarbons, preferably cracked wax, and more preferably cracked wax from a Fischer-Tropsch (FT) process. A process for making olefins by cracking FT products is disclosed in U.S. Pat. No. 6,497,812 which is incorporated herein by reference in its entirety.

In another embodiment of the present invention, the olefinic feed can be a mixture of $C_5+$ olefins where most of the alpha olefins have been removed.

In the process of the present invention another important feedstock is an isoparaffin. The simplest isoparaffin is isobutane. Isopentanes, isohexanes, and other higher isoparaffins are also useable in the process of the present invention. Economics and availability are the main drivers of the isoparaffins selection. Lighter isoparaffins tend to be less expensive and more available due to their low gasoline blend value (due to their relatively high vapor pressure). Mixtures of light isoparaffins can also be used in the present invention. Mixtures such as $C_4$-$C_5$ isoparaffins can be used and may be advantaged because of reduced separation costs. The isoparaffins feed stream may also contain diluents such as normal paraffins. This can be a cost savings by reducing the cost of separating isoparaffins from close boiling paraffins. Normal paraffins will tend to be unreactive diluents in the process of the present invention.

Alkylation conditions for the process of the present invention include a temperature of from about 15 to about 200 degrees C., preferably from about 20 to about 150 degrees C., more preferably from about 25 to about 100, and most preferably from 50 to 100 degrees C.

In order to achieve a high degree of capping (alkylation) of the product an excess of isoparaffin is used. The mole ratio of paraffin to olefin is generally at least 5:1, preferably at least 8:1, more preferably at least 10:1, still more preferably at least 12:1, most preferably at least 14:1. Other techniques can be used to achieve the desired high apparent paraffin to olefin mole ratio; such as use of a multistage process with interstage addition of reactants. Such techniques known in the art can be used to achieve very high apparent mole ratios of isoparaffin to olefin. This helps to avoid oligomerization of the olefin and achieve a high degree of capping (alkylation).

In summary, the potential benefits of the process of the present invention include:
  Reduced capital cost for hydrotreating/hydrofinishing
  Lower operating cost due to reduced hydrogen requirements and extensive hydrogenation requirements
  Improved branching characteristics of the product
  Increased overall molecular weight of the product
  Incorporation of low cost feed (isoparaffins) to increase liquid yield of high value distillate fuel or lubricant components

EXAMPLES

Example 1

Preparation of Fresh 1-Butyl-Pyridinium Chloroaluminate Ionic Liquid 1-butyl-pyridinium chloroaluminate is a room temperature ionic liquid prepared by mixing neat 1-butyl-pyridinium chloride (a solid) with neat solid aluminum trichloride in an inert atmosphere. The syntheses of 1-butyl-pyridinium chloride and the corresponding 1-butyl-pyridinium chloroaluminate are described below. In a 2-L Teflon-lined autoclave, 400 gm (5.05 mol.) anhydrous pyridine (99.9% pure purchased from Aldrich) were mixed with 650 gm (7 mol.) 1-chlorobutane (99.5% pure purchased from Aldrich). The neat mixture was sealed and let to stir at 125° C. under autogenic pressure over night. After cooling off the autoclave and venting it, the reaction mix was diluted and dissolved in chloroform and transferred to a three liter round bottom flask. Concentration of the reaction mixture at reduced pressure on a rotary evaporator (in a hot water bath) to remove excess chloride, un-reacted pyridine and the chloroform solvent gave a tan solid product. Purification of the product was done by dissolving the obtained solids in hot acetone and precipitating the pure product through cooling and addition of diethyl ether. Filtering and drying under vacuum and heat on a rotary evaporator gave 750 gm (88% yields) of the desired product as an off-white shinny solid. $^1$H-NMR and $^{13}$C-NMR were ideal for the desired 1-butyl-pyridinium chloride and no presence of impurities was observed by NMR analysis.

1-Butyl-pyridinium chloroaluminate was prepared by slowly mixing dried 1-butyl-pyridinium chloride and anhydrous aluminum chloride ($AlCl_3$) according to the following procedure. The 1-butyl-pyridinium chloride (prepared as described above) was dried under vacuum at 80° C. for 48 hours to get rid of residual water (1-butyl-pyridinium chloride is hydroscopic and readily absorbs water from exposure to air). Five hundred grams (2.91 mol.) of the dried 1-butyl-pyridinium chloride were transferred to a 2-Liter beaker in a nitrogen atmosphere in a glove box. Then, 777.4 gm (5.83 mol.) of anhydrous powdered $AlCl_3$ (99.99% from Aldrich) were added in small portions (while stirring) to control the temperature. of the highly exothermic reaction. Once all the $AlCl_3$ was added, the resulting amber-looking liquid was left to gently stir overnight under nitrogen in the glove box. The liquid was then filtered to remove any un-dissolved $AlCl_3$. The resulting acidic 1-butyl-pyridinium chloroaluminate was used as the catalyst for the Examples in the Present Application.

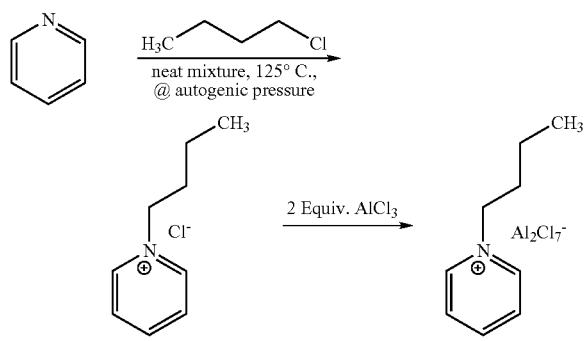

Example 2

Alkylation of 1-decene with iso-butane

In a 300 cc Hastelloy autoclave, 100 gm (1.66 mol.) of liquefied isobutane and 10 gm (0.171 mol.) of 1-decene were added to 40 gm of 1-butyl-pyridinium chloroaluminate. Hydrochloric acid was used in the reaction as a promoter. The autoclave was sealed and the reaction was heated to 50° C. while stirring at ~1000 rpm. The reaction was allowed to stir at 50° C. and at the autogenic pressure for 1 hour. Then, the stirring was stopped and the reaction was cooled to room temperature. The reaction was allowed to settle and the organic layer containing the feed and the products (sitting on the top of the ionic liquid layer) was separated from the ionic liquid by decantation. Excess isobutane was removed on a rotovap and the remaining oily liquid was analyzed by GC and GC-mass spectrometry. Table 1 below shows the GC analysis of the products. GC mass spectrometry of the largest peaks in the GC indicated the products to be saturated $C_{14}$s ($C_{14}H_{30}$; MW=198). It also showed a significant amount of saturated $C_{24}$s with MW of 338.

TABLE 1

| Products | Wt % |
|---|---|
| Below C10s | 7 |
| C10 | 10.4 |
| C14s | 54.3 |
| C20s | 4.9 |
| C24s | 11.6 |
| C30s | 4.3 |
| others | 7.5 |

As shown in Table 1, the expected alkylation product, $C_{14}$s constitute 54% of the products. In addition to 10% $C_{10}$s (possibly the starting decene), we also observed the formation of ~5% dimers ($C_{20}$s) and, not so surprisingly, 11.6% $C_{24}$s which is formed from alkylation of the dimers. We also observed little $C_{30}$s (trimer) and about a little over 10% cracking products (below $C_{10}$s). For the purposes of the present invention, the sum of the $C_{14}$s and the $C_{24}$s in this example indicates the effective yield of capped olefin. In this example, at least 65.9% of the product is capped olefin.

Example 3

Alkylation of 1-decene with iso-pentane

Using the same procedure described above in Example 2, 13 gm of 1-decene was mixed with 101 gm of isopentane in 43 gm 1-butyl-pyridinium chloroaluminate. The reaction mixture (in autoclave) was heated to 50 degrees C. and stirred at 1000 rpm at autogenic pressure of 16 psi for 1 hr. The feed and the products were separated from the ionic liquid by decanting and the products (after removal of excess isopentane) were analyzed by GC and Mass Spectrometry. Table 2 below shows the GC analysis of the products. The major product appeared to be that of saturated $C_{15}$s MW by GC-MS is 212. It also contained 14% of saturated $C_{25}$ (MW=352).

TABLE 2

| Products | Wt % |
|---|---|
| Below C10s | 13 |
| C10 | 9.5 |
| C15s | 38.6 |
| C20s | 3 |
| C25s | 14 |
| C30s | 5.6 |
| others | 7.5 |

As in the alkylation with isobutane, alkylation of 1-decene with isopentane led to the formation of saturated $C_{15}$s. The major peak by GC-MS analysis has a molecular weight of 212 ($C_{15}$ MW=212.4). In addition to the formation of $C_{15}$s, $C_{25}$s were also observed (14%). The formation is $C_{25}$s is due to the alkylation of the 1-decene dimer with isopentane. Dimerisation, trimerisation and cracking products were also observed. For the purposes of the present invention, the sum of the $C_{15}$s and the $C_{25}$s in this example indicates the effective yield of capped olefin. In this example at least 52.6% of the product is capped olefin.

Example 4

Alkylation of 1-Octene with iso-Butane 1-octene was alkylated with isobutane in the 1-butylpyridinium chloroaluminate ionic liquids according to the procedure described in example 2 at an isoparaffin/olefin ratio of 11. The bromine number of the obtained products is 1.6. The Simulated Distillation data of the alkylation products is shown in Table 3.

Example 5

Alkylation of 1-Nonene with iso-Butane

1-Nonene was alkylated with isobutane in the 1-butylpyridinium chloroaluminate ionic liquids according to the procedure described in example 2 at an isoparaffin/olefin ratio of 12. The Simulated Distillation data of the alkylation products is shown in Table 3.

Example 6

Alkylation of 1-Undecene with iso-Butane

1-Undecene was alkylated with isobutane in the 1-butylpyridinium chloroaluminate ionic liquids according to the procedure described in example 2 at an isoparaffin/olefin ratio of 14. The Simulated Distillation data of the alkylation products is shown in Table 3.

Example 7

Alkylation of 1-Dodecene with iso-Butane

1-Dodecene was alkylated with isobutane in the 1-butylpyridinium chloroaluminate ionic liquids according to the procedure described in example 2 at an isoparaffin/olefin ratio of 14. The bromine number of the obtained products is 2.9 (Table 4). The Simulated Distillation data of the alkylation products is shown in Table 3.

Example 8

Alkylation of 1-Hexadecene with iso-Butane

1-Hexadecene was alkylated with isobutane in the 1-butylpyridinium chloroaluminate ionic liquids according to the procedure described in example 2 at an isoparaffin/olefin ratio of 13. The alkylation product has a bromine number of 2.8 (Table 4). The Simulated Distillation data of the alkylation products is shown in Table 3.

Table 3 show the SIMDIST data for the alkylation of 1-octene, 1-nonene, 1-decene, 1-undecene, 1-dodecene, 1-hexadecene with isobutane

TABLE 3

| | $C_8^-/iC_4$ | $C_9^-/iC_4$ | $C_{10}^-/iC_4$ | $C_{11}^-/iC_4$ | $C_{12}^-/iC_4$ | $C_{16}^-/iC_4$ |
|---|---|---|---|---|---|---|
| TBP @ 0.5 | 312 | 300 | 300 | 301 | 301 | 522 |
| TBP @ 5 | 331 | 319 | 332 | 401 | 410 | 590 |
| TBP @ 10 | 361 | 414 | 427 | 485 | 510 | 625 |
| TBP @ 20 | 378 | 439 | 465 | 719 | 702 | 1025 |
| TBP @ 30 | 385 | 798 | 778 | 996 | 985 | 1189 |
| TBP @ 40 | 389 | 1040 | 987 | 1143 | 1136 | 1237 |
| TBP @ 50 | 401 | 1155 | 1116 | 1210 | 1205 | 1264 |
| TBP @ 60 | 512 | 1217 | 1188 | 1235 | 1246 | 1285 |
| TBP @ 70 | 601 | 1263 | 1237 | 1283 | 1277 | 1302 |
| TBP @ 80 | 632 | 1295 | 1237 | 1307 | 1301 | 1319 |
| TBP @ 90 | 739 | 1312 | 1304 | 1332 | 1326 | 1338 |
| TBP @ 95 | 759 | 1340 | 1322 | 1350 | 1344 | 1352 |
| TBP @ 99.5 | 784 | 1371 | 1346 | 1379 | 1374 | 1371 |

The SIMDIST data shown in Table 3 indicates that the alkylation of olefins with isobutane leads to the formation of products with broad boiling ranges. The resulting products include cuts in the fuel boiling range and higher boiling cuts that fall in the lubricant oils boiling range. From these alkylations, it is clear that desired cuts can be obtained by the choice of olefin or olefin mix and by using the appropriate isoparaffin/olefin ratio. Higher isoparaffin/olefin ratios lead to lower boiling products.

Table 4 shows the bromine numbers for some of the alkylation runs shown in Table 3. Table 4 also compares the bromine numbers of the alkylation products of isobutane with 1-octene, 1-decene, 1-dodecene and 1-hexadecene with the bromine numbers of the pure starting olefins.

TABLE 4

| Products/Starting olefins | Bromine Number |
|---|---|
| 1-Octene | 142.4 |
| 1-Octene/iC$_4$ Alkylation | 1.6 |
| 1-Decene | 114 |

TABLE 4-continued

| Products/Starting olefins | Bromine Number |
|---|---|
| 1-Decene/iC$_4$ Alkylation | 2.5 |
| 1-Dodecene | 94.9 |
| 1-Dodecene/iC$_4$ Alkylation | 2.8 |
| 1-Hexadecene | 71.2 |
| 1-Hexadecen/iC$_4$ Alkylation | 2.8 |

The low bromine numbers suggest low olefin concentration in the products and that large portion of these products are paraffinic due to capping off significant portion of the olefins (the starting olefins or their dimers, trimers or higher oligomers). It is evident from the large difference between the bromine numbers of the starting olefins and their alkylation products, that alkylation of alpha olefins in ionic liquids leads to products with high paraffinic character and low olefinicity. This clearly demonstrates the viability of this process for making fuels and lubricant oils with desirable properties.

These experiments clearly show that alkylation of $C_5+$ olefins to make higher alkylates can be done using a chloroaluminate ionic liquid in the presence of a Brönsted acid. Based on these results, one can tailor the reaction and tune the conditions (such as the pressure, temperature, isoparaffins/olefin ratios, amount of catalyst etc.) to optimize the formation of the desired alkylation products.

What is claimed is:

1. A process for making a distillate fuel or lubricant component, comprising: contacting a stream comprising one or more C8+ olefin feed and a stream comprising one or more isoparaffin feed with a catalyst comprising an acidic chloroaluminate ionic liquid comprising 1-butyl-pyridinium chloroaluminate in the presence of a Bronsted acid comprising hydrochloric acid, at alkylation conditions, to form an effluent wherein at least 40 wt % of the effluent is capped olefin.

2. The process of claim 1 wherein at least 50 wt % of the effluent is capped olefin.

3. The process of claim 1 wherein at least a portion of said effluent is used as a fuel or a fuel blendstock.

4. The process of claim 1 wherein at least a portion of said effluent is used as a lubricant base oil or a lubricant blend stock.

5. The process of claim 1 wherein the alkylation conditions comprise a temperature of from about 25 to about 100 degrees C.

6. The process of claim 1 wherein said effluent has a Bromine Number of less than 4.

7. The process of claim 1 wherein the isoparaffin feed is selected from the group consisting of isobutane, isopentane, and a mixture thereof.

8. The process of claim 1 wherein the effluent is subjected to hydrogenation to produce a low olefin lubricant base oil.

9. The process of claim 8 wherein said low olefin lubricant base oil has a Bromine Number of less than 0.2 by ASTM D 1159.

10. The process of claim 1 wherein the stream comprising one or more C8+ olefin feed comprises at least one alpha olefin.

11. The process of claim 10 wherein the stream comprising one or more C8+ olefin feed comprises at least 50 mole % of a single alpha olefin species.

12. The process of claim 10 wherein the stream comprising one or more C8+ olefin feed comprises a mixture of alpha olefins.

13. The process of claim 10 wherein the effluent is subjected to hydrogenation to form a low olefin content alkylate having a Bromine Number of less than 0.4 as measured by ASTM D 1159.

14. The process of claim 1 wherein said effluent has a Bromine Number of less than 3.

15. A process for making a lubricant component, comprising: contacting a stream comprising one or more C8+ olefin feed and a stream comprising one or more isoparaffin feed with a catalyst comprising an acidic chloroaluminate ionic liquid comprising 1-butyl-pyridinium chloroaluminate in the presence of a Bronsted acid comprising hydrochloric acid, at alkylation conditions, to form an effluent; wherein at least 40 wt % of the effluent is capped olefin; and wherein at least a portion of said effluent is used as a lubricant base oil or a lubricant blend stock.

16. The process of claim 15, wherein at least 50 wt % of the effluent is capped olefin.

17. The process of claim 15, wherein the stream comprising one or more isoparaffin feed comprises an isoparaffin selected from the group consisting of isobutane, isopentane, and a mixture thereof.

18. The process of claim 15, wherein the alkylation conditions comprise a temperature of from about 25 to about 100 degrees C.

19. The process of claim 15, wherein the stream comprising one or more C8+ olefin feed comprises a mixture of alpha olefins.

20. The process of claim 15, wherein the stream comprising one or more C8+ olefin feed comprises at least one alpha olefin.

* * * * *